(12) United States Patent
Shankarappa et al.

(10) Patent No.: US 7,337,651 B2
(45) Date of Patent: Mar. 4, 2008

(54) METHOD FOR PERFORMING MODEL BASED SCANPLAN GENERATION OF A COMPONENT UNDER INSPECTION

(75) Inventors: Suneel Tumkur Shankarappa, Bangalore (IN); William Stewart McKnight, Hamilton, OH (US); Vamshi Krishna Reddy Kommareddy, Bangalore (IN); Ui Won Suh, Cincinnati, OH (US); Mandar Diwakar Godbole, Bangalore (IN); Anjani Narendra Schrad, West Chester, OH (US); Prafull Sharma, Indore (IN)

(73) Assignee: General Electric Company, Niskayuna, NY (US)

( * ) Notice: Subject to any disclaimer, the term of this patent is extended or adjusted under 35 U.S.C. 154(b) by 291 days.

(21) Appl. No.: 11/100,106

(22) Filed: Apr. 5, 2005

(65) Prior Publication Data

US 2006/0224348 A1    Oct. 5, 2006

(51) Int. Cl.
 *G01B 3/30* (2006.01)
(52) U.S. Cl. ...................................... 73/1.79
(58) Field of Classification Search ................... 73/1.79
 See application file for complete search history.

(56) References Cited

U.S. PATENT DOCUMENTS

| | | | |
|---|---|---|---|
| 5,058,433 A * | 10/1991 | Wilson et al. ................. | 73/651 |
| 5,430,376 A | 7/1995 | Viertl | |
| 6,220,099 B1 | 4/2001 | Marti et al. | |
| 6,637,266 B1 | 10/2003 | Froom | |
| 2003/0089183 A1 | 5/2003 | Jacobsen et al. | |
| 2004/0003647 A1 * | 1/2004 | Nashiki et al. ............... | 73/1.79 |
| 2004/0153260 A1 | 8/2004 | Suh et al. | |
| 2004/0178790 A1 | 9/2004 | Gifford et al. | |
| 2004/0244464 A1 * | 12/2004 | Hajdukiewicz et al. ...... | 73/1.79 |
| 2006/0213250 A1 * | 9/2006 | Vaccaro et al. ............... | 73/1.86 |
| 2006/0266100 A1 * | 11/2006 | McMurtry et al. ........... | 73/1.79 |

FOREIGN PATENT DOCUMENTS

JP        10-318865    * 12/1998

OTHER PUBLICATIONS

H. W. Ma et al., "Research on a Ultrasonic NDT System for complex surface parts," Journal of Materials Processing Technology, vol. 129, Oct. 11, 2002, pp. 667-670.
EP Search Report, EP06251683, Jul. 6, 2006.
C.N. Hebbalae et al., "Automatic Generation and Execution of Eddy Current Scan Plans," Review of Progress in Non Destructive Evaluation, vol. 14, 1995, ISBN 0306450623, pp. 299-306.

* cited by examiner

*Primary Examiner*—Robert Raevis
(74) *Attorney, Agent, or Firm*—Penny A. Clarke; Patricia K. Patnode (57) ABSTRACT

A method for generating a scanplan for inspection of a component is provided. The method includes loading a geometric model of the component and generating the scanplan of the component based on the geometric model and at least one scanning parameter. A method of inspecting a component is also provided and includes loading a geometric model of the component, generating a scanplan of the component based on the geometric model and at least one scanning parameter, mounting the component on an inspection system manipulator and inspecting the component including moving an inspection probe relative to the component using the scanplan.

21 Claims, 14 Drawing Sheets

METHOD FOR PERFORMING MODEL BASED SCANPLAN GENERATION OF A COMPONENT UNDER INSPECTION

BACKGROUND

The invention relates generally to non-destructive inspection techniques and more particularly to a method for performing model based scanplan generation of a component under inspection.

Eddy current (EC) inspection is a non-destructive technique used to inspect metal components and other components with one or more metal layers or regions (collectively "metal components.") In certain applications, eddy current inspection techniques are used for measuring residual stress, density and degrees of heat treatment in metal components. These techniques are also used to detect physical defects or abnormalities on or near metal surfaces, such as, dents, bumps, or minute cracks in the material.

Non-destructive inspection of a component typically requires the use of a mechanical scanner to manipulate a probe in a particular scan pattern on the surface of the component being inspected. The component to be inspected is loaded onto the mechanical scanner, and the probe is moved to desired locations on the component to generate the scan pattern or the scanplan for a given surface on the component. In a typical operation of a mechanical scanner, an appropriate probe configuration is chosen and loaded onto the mechanical scanner. A semi-automatic software script then records appropriate coordinates on the surface of the component based on the movement of the probe. A scanplan is generated by repeating the procedure for all surfaces on the component to be inspected. The generated scanplan may further be validated, and the validation also is generally performed on the mechanical scanner.

The above procedures of generation and validation of the scanplan, however, are machine specific and have to be repeated each time a different mechanical scanner is used, even if the same component is being inspected. In addition, the generation and validation of the scanplan for complex parts having complex geometrical shapes typically involves the effort and the skill set of the operator since the geometry of the component under inspection is generally not considered in generating and qualifying the scanplan. Therefore, a number of hours may be spent generating and validating the scanplan for such complex parts, since a significant amount of time is needed to set up the mechanical scanner and the component to be inspected, every time a scanplan is generated. The generated scanplan is then used to perform component inspections.

It would therefore be desirable to generate and validate a scanplan of a component, offline, thereby saving machine time and overall inspection time. It would also be desirable to generate a scanplan of a component based on the geometric characteristics of the component. In addition, it would be desirable to generate a generic scanplan for a component, regardless of the type of mechanical scanner that will be used to perform the component inspection.

BRIEF DESCRIPTION

Embodiments of the present invention address these and other needs. In one embodiment, a method for generating a scanplan for inspection of a component is provided. The method includes loading a geometric model of the component and generating the scanplan of the component based on the geometric model and at least one scanning parameter.

In another embodiment, a method of inspecting a component is provided. The method includes generating a scanplan by loading a geometric model of the component and generating the scanplan of the component based on the geometric model and at least one scanning parameter. The method further includes mounting the component on an inspection system manipulator and inspecting the component, the inspection including moving an inspection probe relative to the component using the scanplan.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Disclosed herein, is a method for performing model based scanplan generation of a component under inspection. The disclosed method generates and validates the scanplan of a component, offline, based on geometric characteristics of the component. In particular, and as will be described in greater detail below, the disclosed method loads a geometric model of the component onto a model of an inspection system manipulator and generates the scanplan of the component based on features in the geometric model and one or more scanning parameters. Embodiments of the present invention offer several advantages including minimized machine and inspection time and enhanced machine utility and productivity. In addition, the generated scanplan in accordance with embodiments of the present invention is not machine specific and can be used on different inspection systems for performing component inspections. The invention can be used with a variety of components, examples of which include without limitation turbine disks, blades, spools, and in general, any axis-symmetric part.

Figure 1:
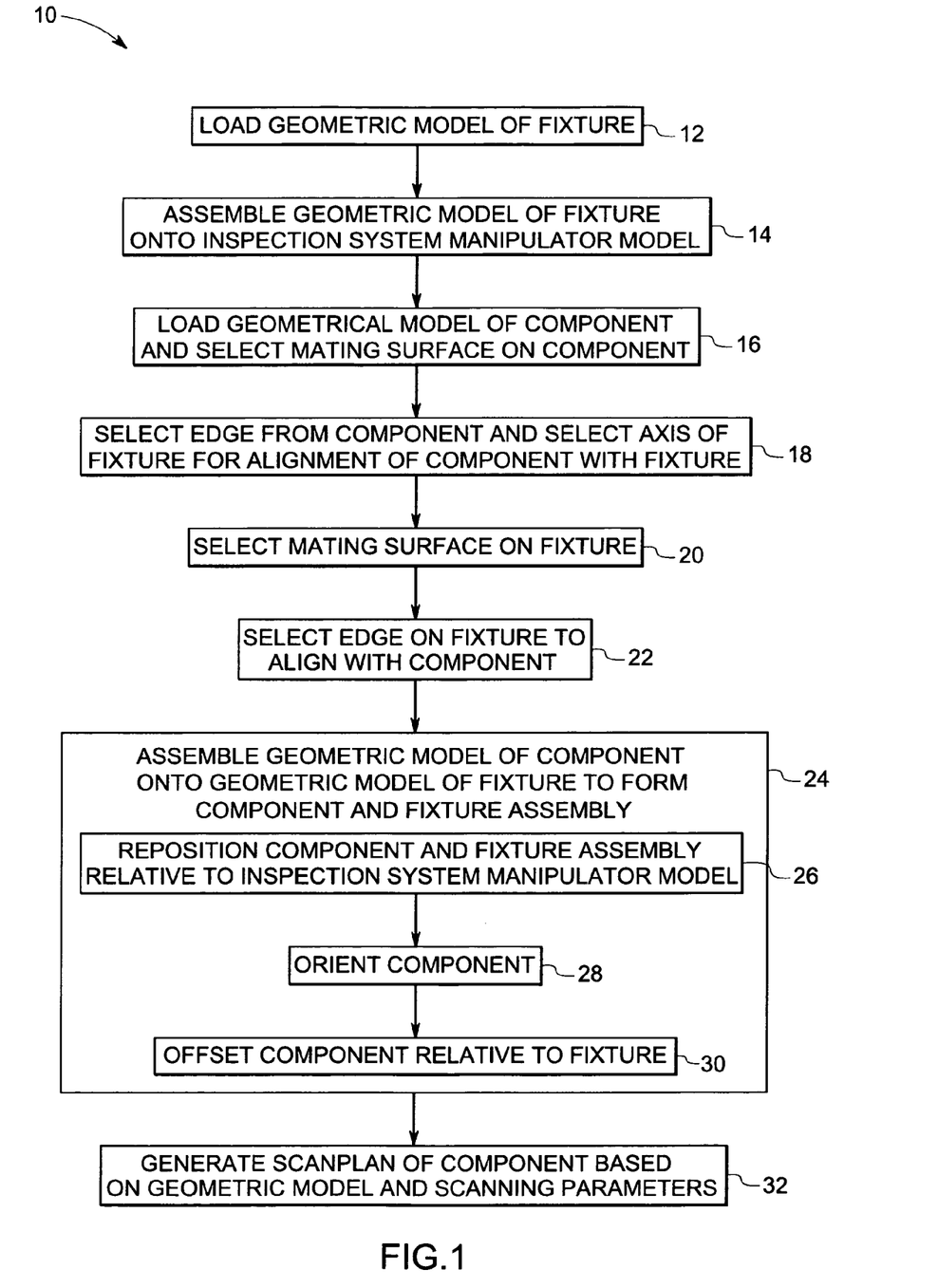
FIG. 1 is a flowchart of exemplary logic including exemplary steps for generating a scanplan for inspection of a component, in accordance with one embodiment of the present invention.

FIG. 1 is a flowchart 10 of exemplary logic including exemplary steps for generating a scanplan for inspection of a component, in accordance with one embodiment of the present invention. In a specific implementation of the present embodiment, and as will be described in greater detail below, the inspection system targeted to execute the scanplan is modeled using the UNIGRAPHICS® graphical user interface (GUI) software and is generally referred to as an inspection system manipulator. Unigraphics® is a registered trademark of the Electronic Data Systems Corporation. As used herein, the term "scanplan" refers generally to the collection of software and machine instructions used to provide the motion control, data acquisition and operator messages associated with scanning a probe over the component under inspection at the prescribed speed, index value and orientation.

Figure 8:
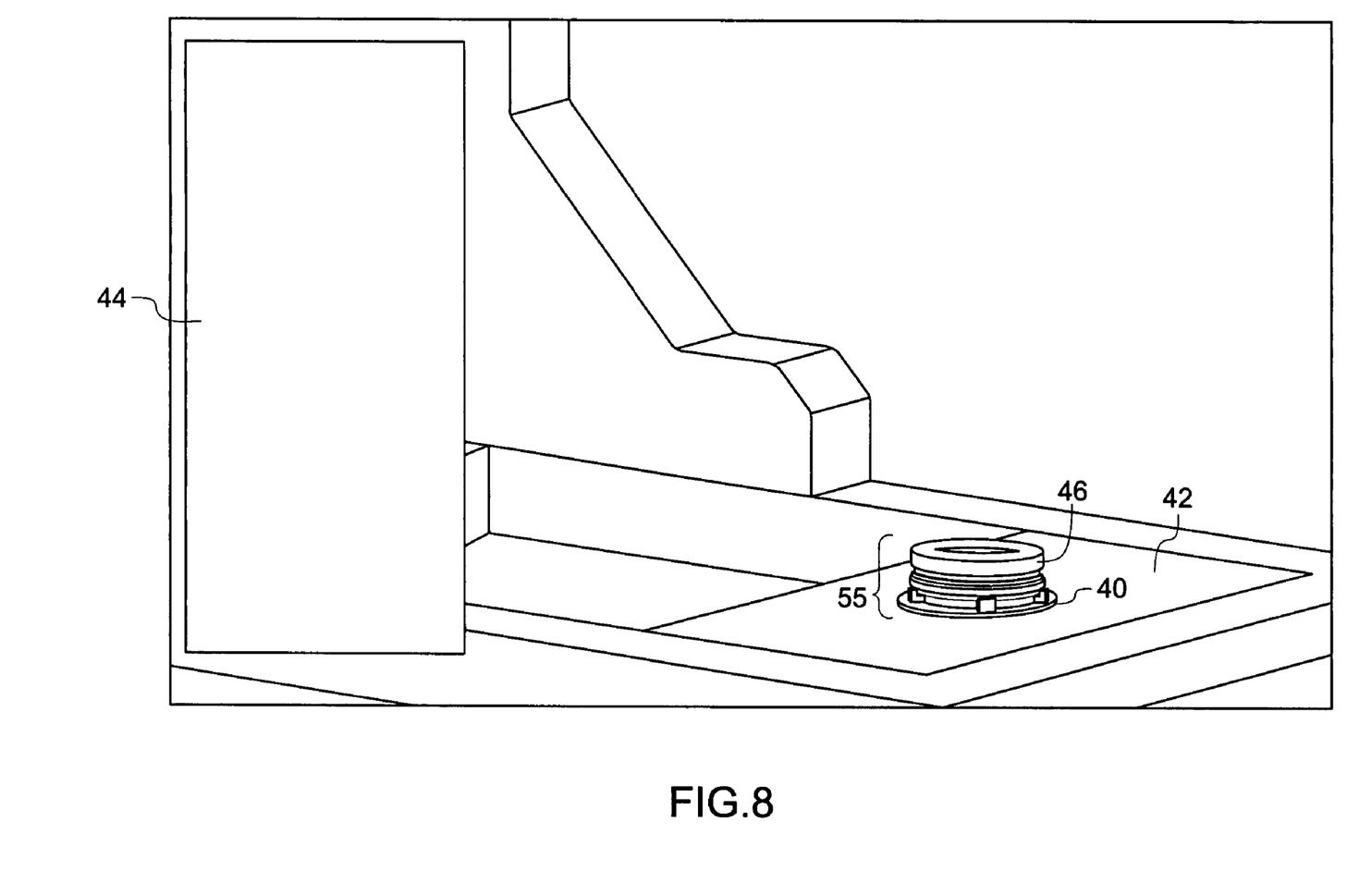
FIG. 8 is an exemplary illustration of a component and fixture assembly.

Referring to FIG. 1, in step 12, a geometric model of the fixture is initially loaded. In accordance with the present embodiment, a component 46 under inspection is held in a fixture 40. FIG. 8 is an exemplary illustration of a component and fixture assembly. In a particular embodiment, the geometric model is a Computer Aided Design (CAD) model of the fixture. As will be appreciated by those skilled in the art, a fixture may be used to provide accurate positioning and rotational orientation for the component.

Figure 2:
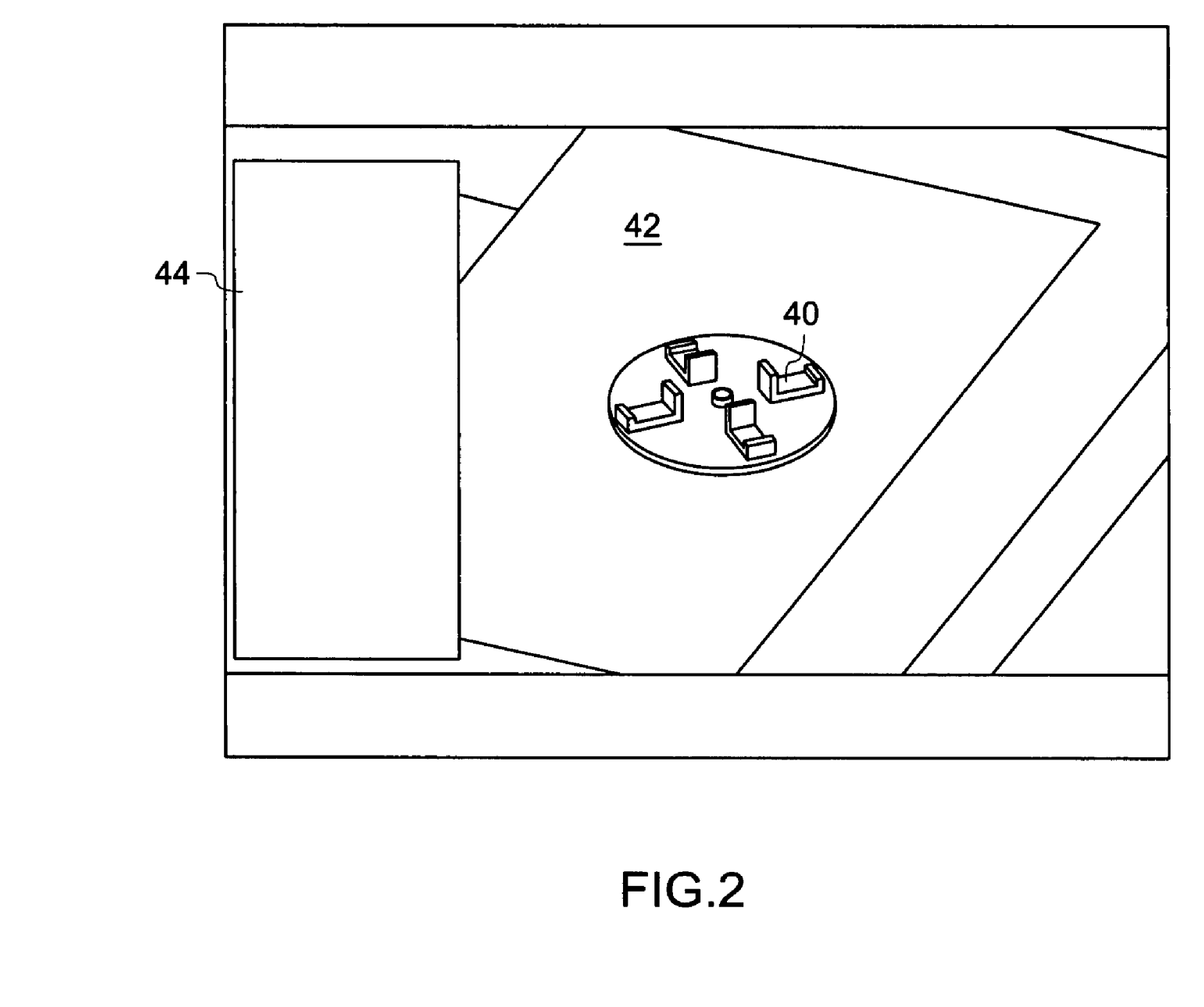
FIG. 2 is an illustration of a fixture assembly mounted onto a model of an inspection system manipulator.

In step 14, the geometric model of the fixture is assembled onto the model of the inspection system manipulator. Further, in this step, a surface on the fixture to be mated with the inspection system manipulator model and a surface on the inspection system manipulator model are also determined. FIG. 2 is an illustration of a fixture assembly mounted onto an inspection system manipulator model. In a particular implementation of the present invention, the geometric model of the fixture 40 may be automatically assembled onto the inspection system manipulator model 42 using the UNIGRAPHICS Open API program. In particular, a dialog box 44 may further facilitate the selection of a desired fixture to be assembled onto the inspection system manipulator model.

Figure 3:
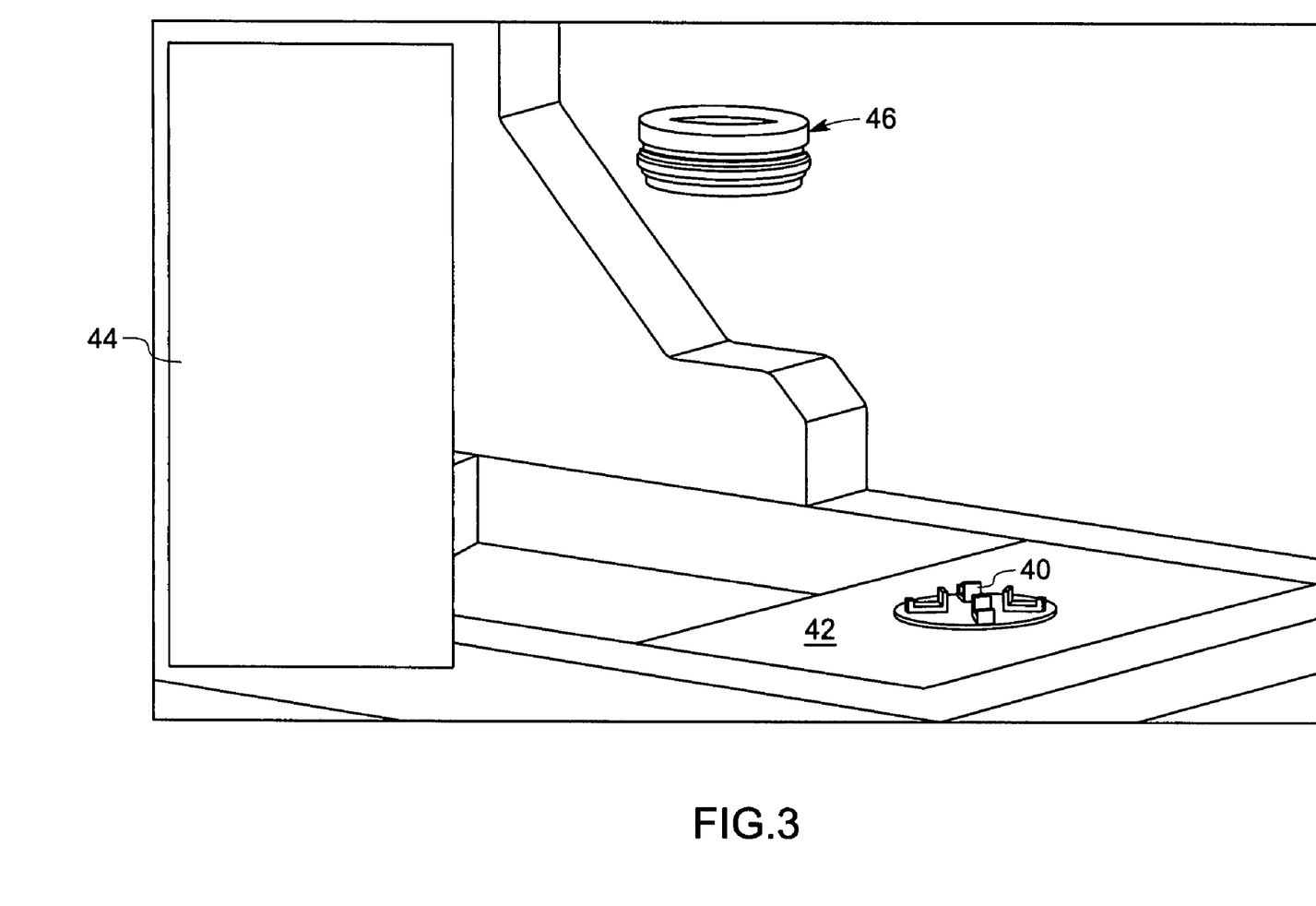
FIG. 3 is an illustration showing the loading of a geometric model of a component under inspection.
Figure 4:
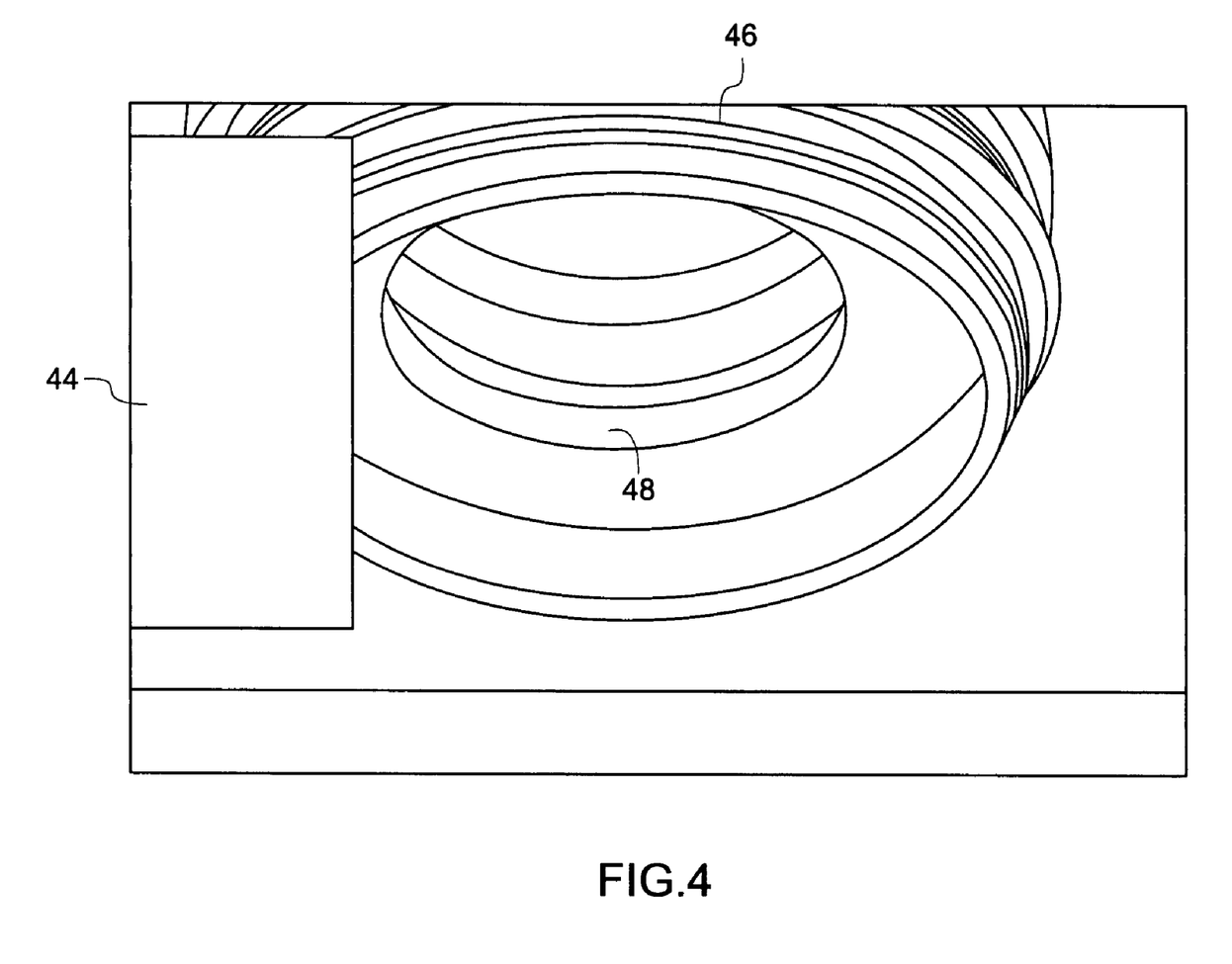
FIG. 4 is an illustration of a selected mating surface on the geometric model of the component shown in FIG. 3.

In step 16, a geometric model of the component is loaded and a mating surface on the component is selected. FIG. 3 is an illustration showing the loading of a geometric model of a component under inspection. In a particular implementation of the present invention, the geometric model of the component 46 may be automatically loaded using the UNIGRAPHICS® Open API development. For the exemplary embodiment shown in FIG. 3, a dialog box 44 facilitates the selection and loading of the geometric model 46. In a particular embodiment, the geometric model is a CAD model of the component under inspection. Similarly, FIG. 4 shows a selected mating surface 48 on the geometric model of the component 46.

Figure 5:
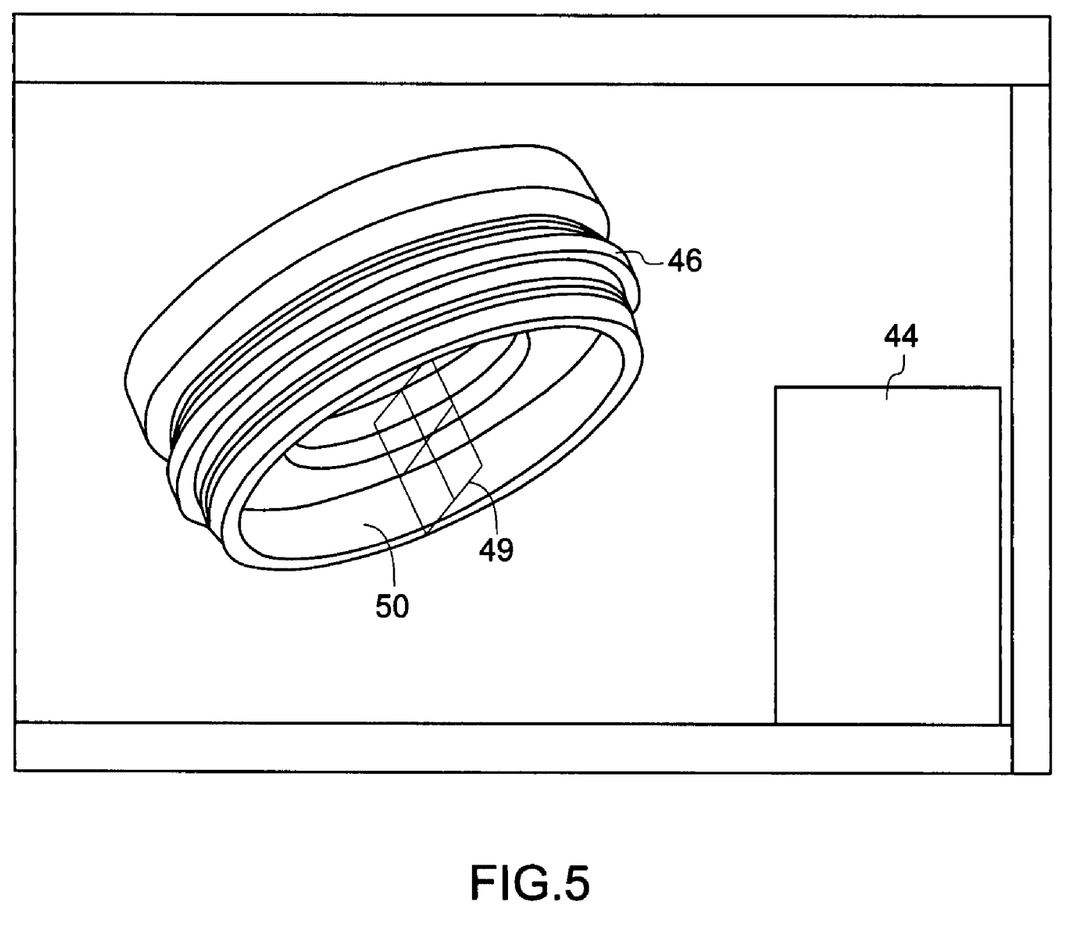
FIG. 5 is an illustration of a selected edge on the geometric model of the component shown in FIG. 3.

In step 18, an edge 50 on the component and an axis 49 of the fixture for alignment of the component with the fixture, is selected. FIG. 5 is an illustration of a selected edge on the geometric model of the component shown in FIG. 3. In a particular implementation of the present invention, an edge 50 on the component 46 may be selected using the UNIGRAPHICS® Open API program. In general, for an axially symmetric component, any edge on the component may be selected to align the axis of the component and the fixture. For the exemplary embodiment shown in FIG. 5, a dialog box 44 enables the selection of a desired edge on the component.

Figure 6:
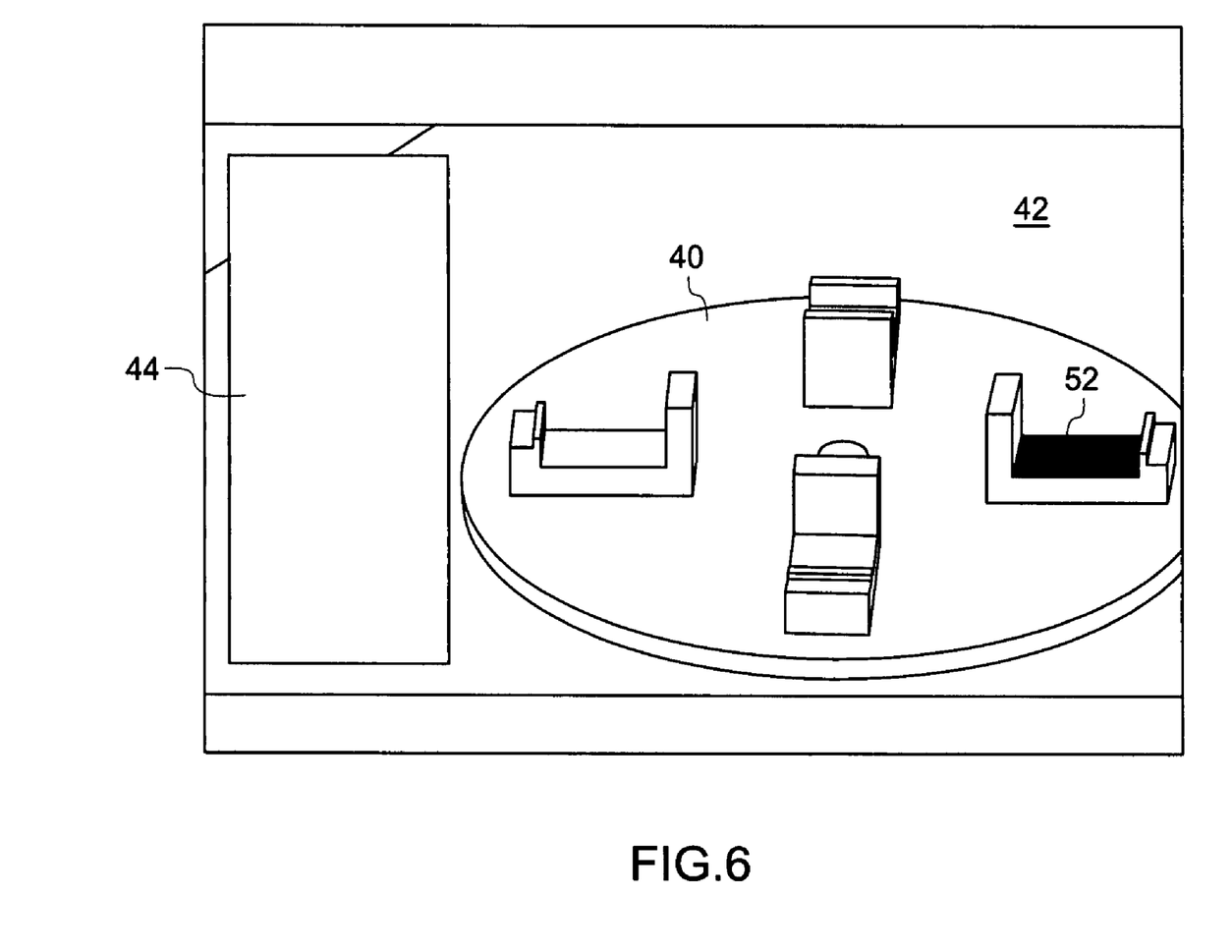
FIG. 6 is an illustration of a selected mating surface on the fixture shown in FIG. 2.

In step 20, a mating surface 52 on the fixture is selected. FIG. 6 is an illustration of a selected mating surface on the fixture. In a particular implementation of the present invention, a mating surface 52 on the fixture may be selected using the UNIGRAPHICS® Open API program. In addition, for the exemplary embodiment shown in FIG. 6, a dialog box 44 enables the selection of a particular mating surface on the fixture.

Figure 7:
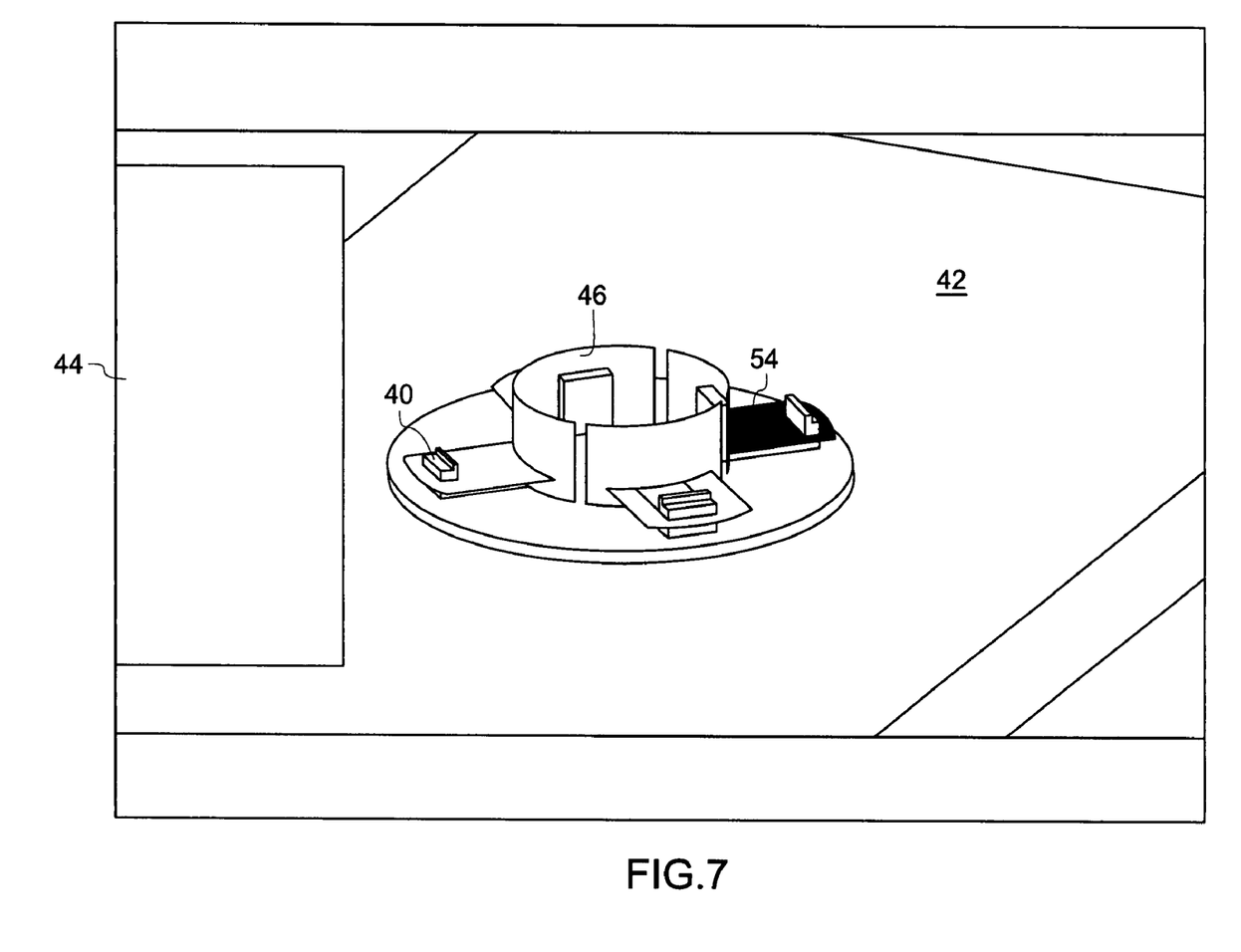
FIG. 7 is an illustration of a selected edge on the fixture shown in FIG. 2.

In step 22, the edge 54 on the fixture for alignment of the component, is selected. FIG. 7 is an illustration of a selected edge on the fixture. In a particular implementation of the present invention, an edge 54 on the fixture to align with the component 46 may be selected using the UNIGRAPHICS® Open API program. In addition, for the exemplary embodiment shown in FIG. 7, a dialog box 44 enables the selection of a desired edge on the fixture.

Figure 9:
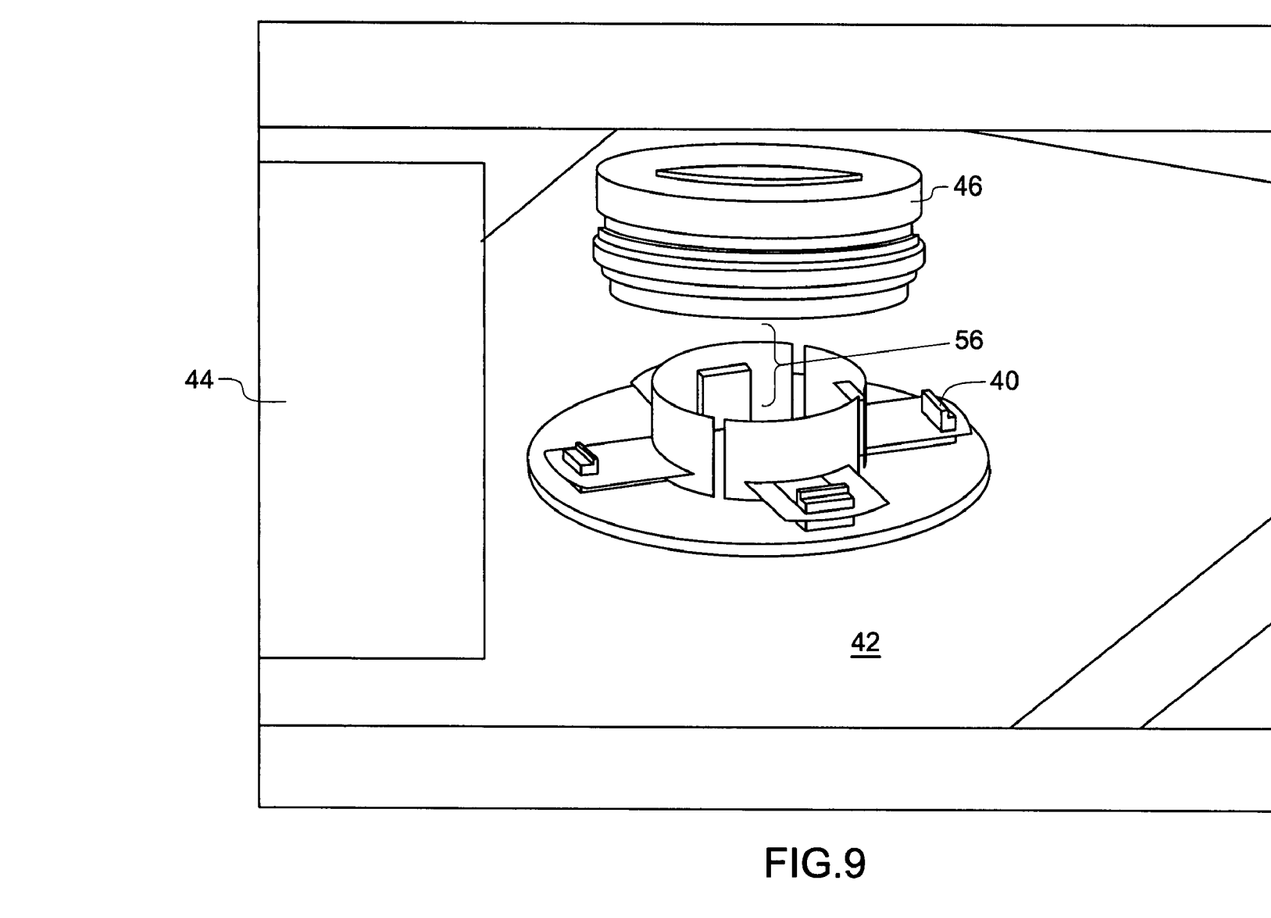
FIG. 9 is an illustration of a component that is offset by a desired distance above the fixture.

In step 24, the geometric model of the component, generated in step 16 is assembled onto the geometric model of the fixture, generated in step 12, to form a component and fixture assembly, using the mating surfaces of the fixture and of the component, as described above. FIG. 8 is an exemplary illustration of an assembled component and fixture assembly 55. In addition, a dialog box 44 implemented using the UNIGRAPHICS® Open API program, enables the automatic assembly of the component onto the fixture. In a particular aspect of the present technique, step 24 may additionally include repositioning the component and fixture assembly relative to the inspection system manipulator model in step 26, orienting the component in step 28 and offsetting the component relative to the fixture in step 30. In accordance with this aspect, the component may further be oriented to any desired position, by selecting an appropriate surface on the component to be assembled onto the fixture. The component may also be offset above the fixture by a desired distance. This enables the selection of a virtual fixture when a geometric model is not available. FIG. 9 is an illustration of a component 46 that is offset by a desired distance 56 above the fixture 40. In addition, for the exemplary embodiment shown in FIG. 9, a dialog box 44, implemented using the UNIGRAPHICS® Open API program, enables the selection of a desired offset distance.

In step 32, the scanplan of the component is generated based on the geometric model and one more scanning parameters, as will be described in greater detail in the subsequent paragraphs.

Figure 10:
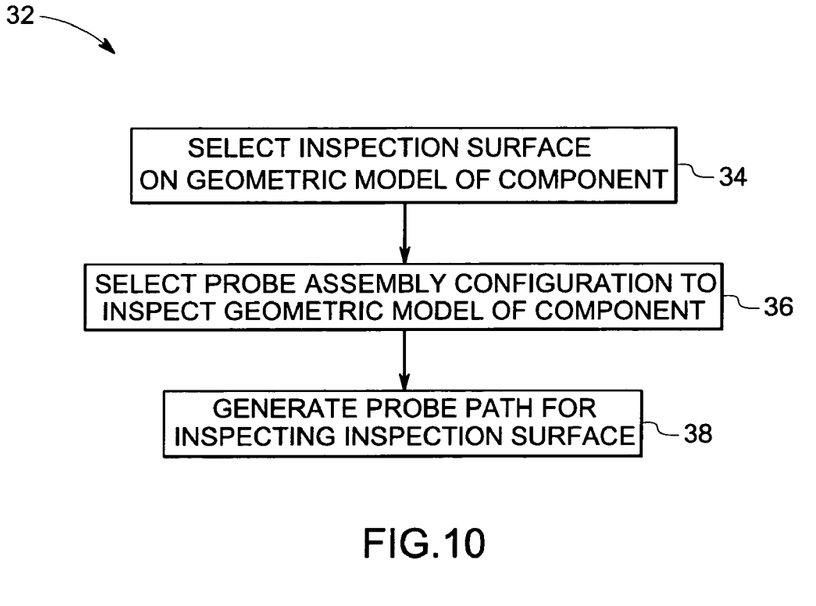
FIG. 10 is a flowchart of exemplary logic including exemplary steps for performing certain steps in the flowchart illustrated in FIG. 1.
Figure 11:
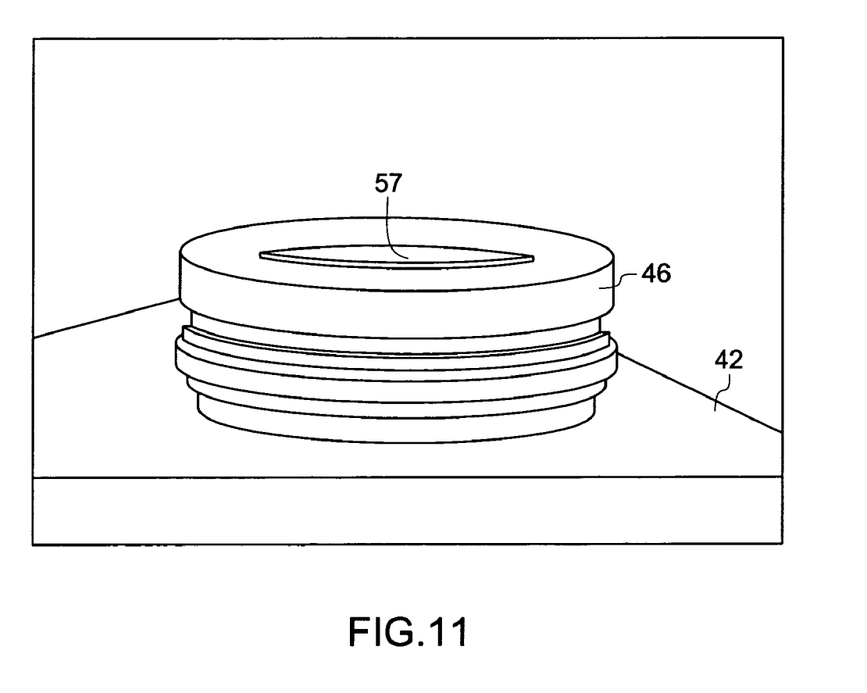
FIG. 11 is an exemplary illustration of a selected surface on the geometric model.

FIG. 10 is a flowchart of exemplary logic including exemplary steps for performing step 32 of FIG. 1. In step 34, one or more inspection surfaces on the geometric model of the component are selected. FIG. 11 is an exemplary illustration of a selected surface 57 on the geometric model. In a particular implementation of the present invention, a surface 57 on the fixture may be automatically selected using the UNIGRAPHICS® GUI software. A dialog box 44 further enables the automatic selection of different surfaces on the geometric model of the component. In a particular embodiment, step 34 further includes the steps of selecting one or more scanning parameters, deselecting the inspection surfaces, breaking up the inspection surfaces and selecting an inspection area on the geometric model of the component. Exemplary scanning parameters include geometric parameters and non-geometric parameters. Exemplary geometric parameters include a number of surface specific inspection parameters, such as parameters for deselecting one or more inspection surfaces and breaking up of one or more inspection surfaces. Exemplary non-geometric parameters include a scanning velocity parameter, a step-size (index) parameter, an index direction parameter, an axis tilt parameter and a probe orientation parameter. These parameters are selected for all the surfaces under inspection. In a particular embodiment of the present invention, a UNIGRAPHICS Open API program may be developed to enable the selection of desired parameters, the de-selection of desired inspection surfaces, the break up of desired inspection surfaces and the selection of a desired inspection area on the geometrical model of the component.

Figure 12:
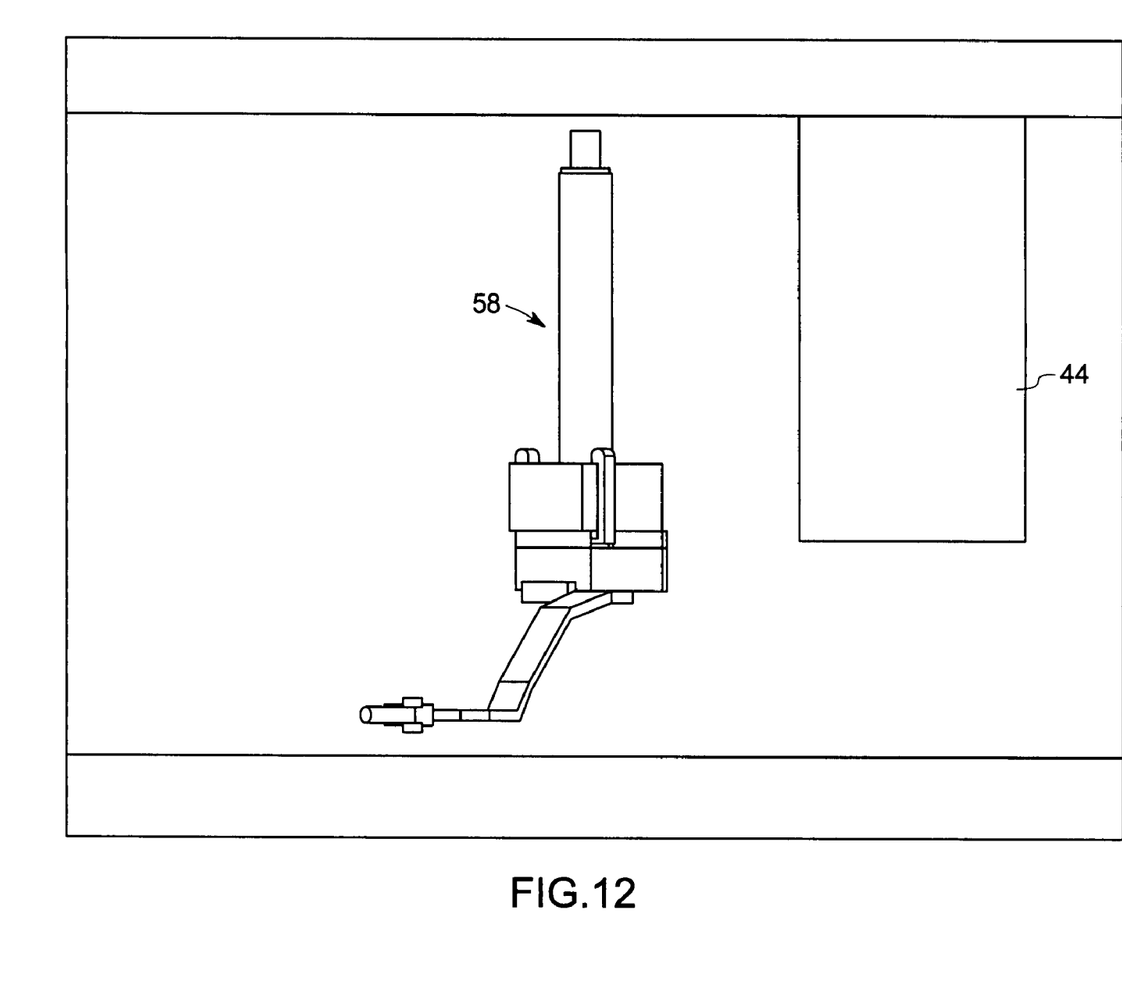
FIG. 12 is an exemplary illustration of a probe assembly configuration.

In step 36, a probe assembly configuration to inspect the geometric model of the component is selected. In accordance with one embodiment, step 36 includes the steps of selecting a probe, a probe holder and a stem, selecting an appropriate probe configuration and assembling the probe based upon the selected probe configuration. FIG. 12 is an exemplary illustration of a probe assembly configuration. In a particular implementation of the present invention, the probe assembly 58 may be automatically assembled using the UNIGRAPHICS® Open API program. A dialog box interface 44, shown without details in FIG. 12 enables the selection of a variety of probe configurations, as well as the selection of an appropriate probe assembly configuration, which may include a probe, a probe holder and a stem section to assemble the probe.

Figure 13:
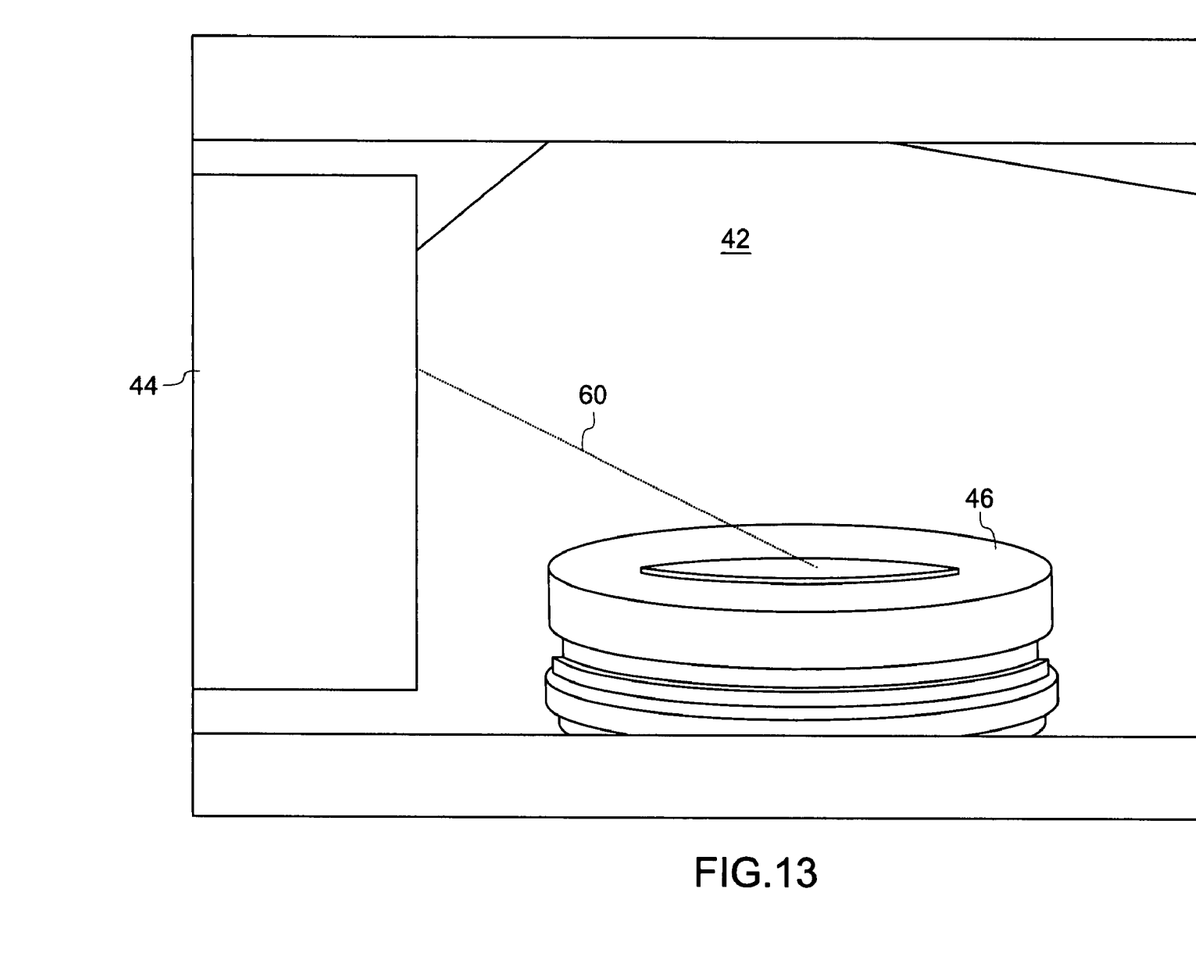
FIG. 13 is an exemplary illustration of a probe path for a selected inspection surface.

In step 38, a probe path for inspecting the inspection surfaces is generated. This step further includes selecting one or more inspection parameters such as, a desired step size value and a step direction for the selected inspection surfaces. In addition, this step includes selecting a number of intermediate points to guide the probe along a probe path. This step further includes visualizing and validating the probe path for a selected inspection surface based on the selected inspection parameters for that surface and the selected probe assembly configuration. FIG. 13 is an exemplary illustration of a probe path for a selected inspection surface. In a particular embodiment of the present invention, the probe path 60 for a selected inspection surface may be displayed using the UNIGRAPHICS® GUI software. Also, for the exemplary embodiment shown in FIG. 13, a dialog box interface 44 enables the display of the probe path for a selected inspection surface.

In certain embodiments, step 38 includes generating a collision free probe path wherein the probe path includes the SAFE, INIT, BEGIN and End Cartesian coordinates. As used herein, the "SAFE" coordinate refers to the location of the probe just above the component under inspection, INIT refers to the location of the probe near the feature to be inspected and the BEGIN and END coordinates encompass the surface of the component under inspection. Further, in this embodiment, an alert may be displayed using the UNIGRAPHICS® GUI software when a collision occurs between the probe and any of the components loaded onto the assembly.

In certain embodiments, step 38 also includes simultaneously modifying the probe path by adjusting the coordinate positions along the probe path. In particular, the coordinates of the probe path may be modified by providing probe rotation or orientation along the principle coordinate axes X, Y Z, along the lines of probe orientation (or alternatively, the probe increment axis A), along the probe rotation axis B, along the component axis or rotating table rotation, C and along the probe tilt axis, U. With respect to the model of the inspection system manipulator disclosed in embodiments of the present invention, the coordinate X, Y and Z, axes are standard linear plane configurations. The U-axis is attached to the end of the Z-axis and incorporates an A-axis or slide table, which traverses along the angular axis established by U. The B-axis is mounted on the U and A axes and provides both spindle and position motions of the probe when it is inserted into the collect of the B-axis probe scanner positioner. The C-axis is center-referenced to the Y-axis and is capable of either spindle or positioning motions.

The scanplan of the geometric model is then generated based on the selected inspection surfaces, the scanning parameters and the probe assembly.

In another embodiment of the present invention, a method for validating a scanplan to be used in the inspection of a component is provided. In accordance with a particular embodiment of the present invention, the inspection system manipulator used to validate the scanplan is modeled using the UNIGRAPHICS® GUI software.

Figure 14:
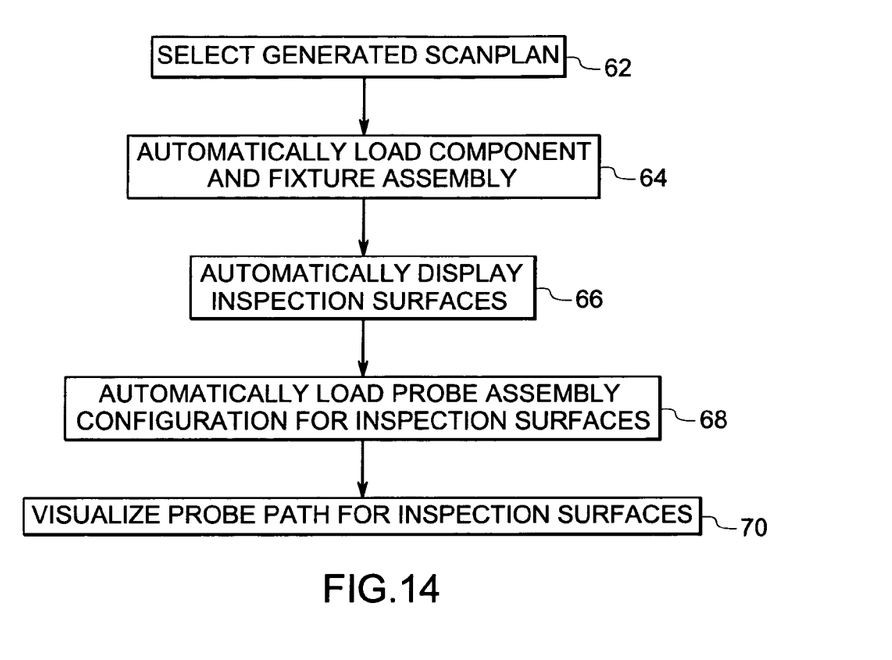
FIG. 14 is a flowchart of exemplary logic including exemplary steps for performing validation of a generated scanplan.

FIG. 14 is a flowchart illustrating exemplary steps for performing validation of a generated scanplan based on the fixture, the component, the probe assembly and the scanplan as discussed with respect to FIG. 1 above. In step 62, the generated scanplan is selected. A plurality of information from the scanplan such as, the SAFE, INIT, BEGIN and END coordinates, component and fixture assembly information, and probe configuration information is extracted from the scanplan. In one embodiment, the above information may be stored in a database and automatically retrieved to perform the validation of the generated scanplan. In particular, in this step, one or more scanning parameters for one or more inspection surfaces are automatically retrieved from the scanplan. As mentioned above, exemplary scanning parameters include surface specific inspection parameters. Further, in this step, the scanning parameters are automatically associated with their respective inspection surfaces.

In step 64, the component and fixture assembly is automatically loaded from the generated scanplan.

Figure 15:
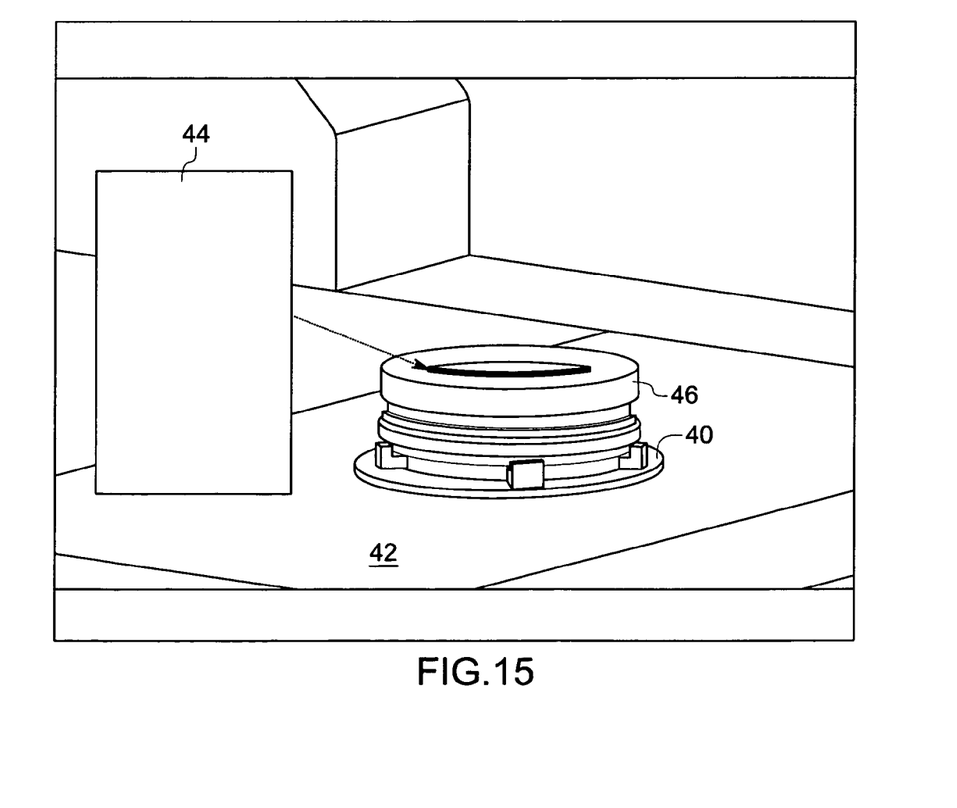
FIG. 15 is an exemplary illustration of a set of displayed surfaces.

In step 66, the inspection surfaces are automatically displayed. FIG. 15 is an exemplary illustration of a set of displayed surfaces. In a particular implementation of the present invention, a dialog box interface 44 implemented using the UNIGRAPHICS® Open API program enables the automatic display of the scanning parameters and the inspection surfaces along with their respective inspection coordinates such as SAFE, INIT, BEGIN and END. In certain embodiments of the present invention, step 66 also includes deselecting one or more of the displayed inspection surfaces.

In step 68, an appropriate probe assembly configuration is automatically loaded for the inspection surfaces. A dialog box interface implemented using the UNIGRAPHICS® Open API program may further enable the automatic loading of the probe assembly configuration for the selected inspection surface.

Figure 16:
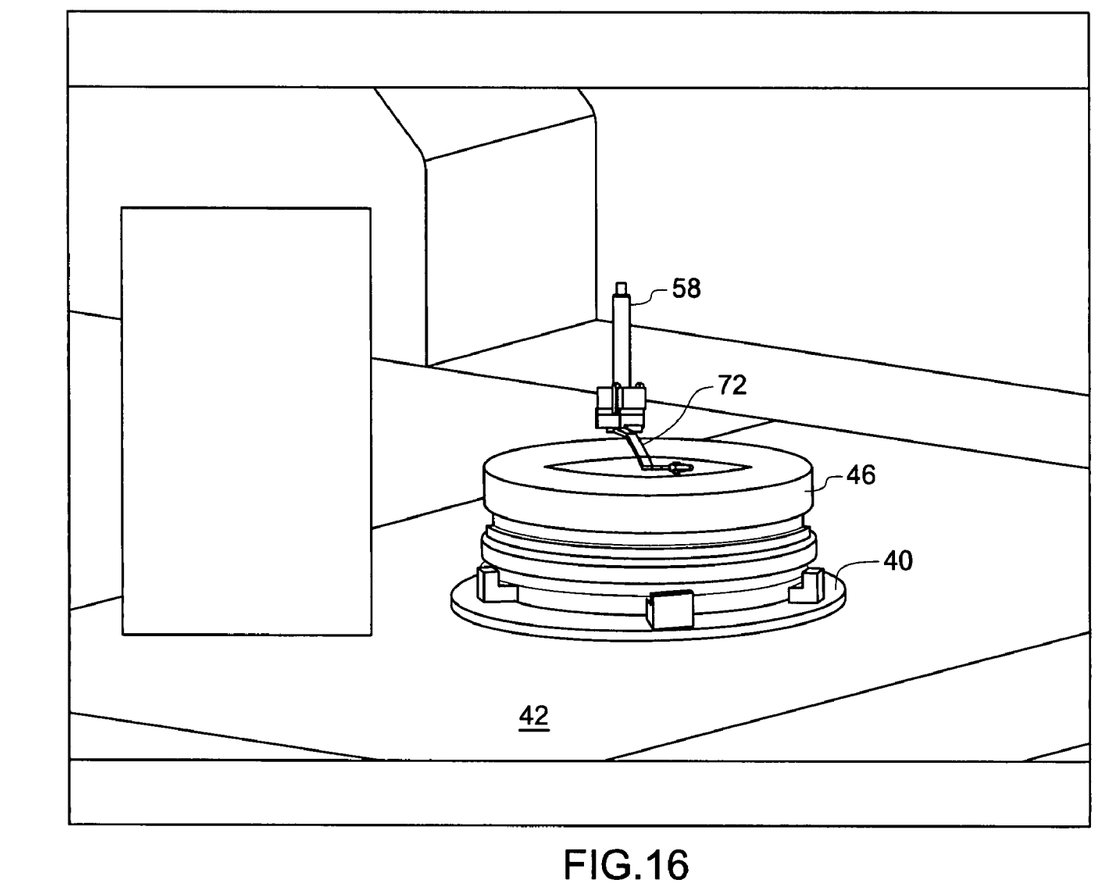
FIG. 16 is an exemplary illustration showing the simulation of a probe path.

In step 70, the probe path for the inspection surfaces is visualized, based on the scanning parameters and the probe assembly configuration. Further, the probe path may be visualized for each selected inspection surface, thereby validating the scanplan for inspection area overlaps and collision avoidance surfaces. FIG. 16 is an exemplary illustration of the simulation of a probe path. In a particular implementation of the present invention, and as shown in FIG. 16, the simulation of a probe path, indicated by the reference numeral 72 may be performed using the UNIGRAPHICS® GUI software. Further, in this implementation, programming errors may be highlighted if the probe paths interfere with the UNIGRAPHICS® GUI defined surfaces of the component, fixture or inspection system.

In step 72, a checklist is generated. The checklist includes information regarding tape checks, component loading information, unloading information for calibration, various steps describing inspection checks, operator details etc.

Following the generation and validation of the scanplan, the component under inspection may be mounted onto an inspection system manipulator (for example, the component may be mounted to a fixture, which is mounted on the inspection machine) and inspected using an inspection probe. The inspection includes moving an inspection probe relative to the component using the scanplan. Examples of the inspection probe include, without limitation, an eddy current probe and an ultrasonic probe.

The method of performing scanplan generation and validation as disclosed in embodiments of the present invention may be applied in any probe based component scanning application, such as ultrasound and optical applications, telemetry and surgical operations. The model of the inspection system manipulator used to generate the scanplan in accordance with embodiments of the present invention is an integration of multiple hardware components and software tools and is capable of detecting minute surface and near-surface flaws in symmetric or complex shaped electrically conductive materials, thereby improving inspection reliability and productivity. Further, in accordance with the present invention, the generation of the scanplan program and its validation can be performed offline, and does not require the use of an inspection machine or scanner to generate and validate the scanplan, thereby minimizing machine time. Also, the scanplan in accordance with embodiments of the present invention is generated based on a generic point on the inspection system manipulator model. This facilitates precise and consistent performance on multiple systems in diverse venue inspection system manipulators using the same scan plan. By computing the scan plan parameters and data relative to this generic point, it is only necessary to reference the generic point to assure the precise reproduction of the programmed inspection using the same scanplan. Therefore, using the above technique, the requirement of an accurate and precise alignment of each inspection system relative to each other to assure comparable performance maybe eliminated.

As will be appreciated by those skilled in the art, the embodiments and applications illustrated and described above will typically include or be performed by appropriate executable code in a programmed computer. Such programming will comprise a listing of executable instructions for implementing logical functions. The listing can be embodied in any computer-readable medium for use by or in connection with a computer-based system that can retrieve, process and execute the instructions.

In the context of the present technique, the computer-readable medium is any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for generating a scanplan for inspection of a component, the method comprising:
   loading a geometric model of the component;
   generating the scanplan of the component based on the geometric model and at least one scanning parameter; and
   validating the scanplan, wherein validating the scanplan comprises:
   automatically retrieving one or more scanning parameters and one or more inspection surfaces from the generated scanplan,
   automatically loading a component and fixture assembly from the generated scanplan,
   automatically displaying the one or more inspection surfaces, automatically loading a probe assembly configuration for the one or more inspection surfaces, and
   visualizing a probe path for the one or more inspection surfaces, based on the one or more scanning parameters and the probe assembly configuration.

2. The method of claim 1, wherein the component is held in a fixture, the method further comprising loading a geometric model of the fixture, wherein generating the scanplan is further based on the geometric model of the fixture.

3. The method of claim 2, further comprising:
   assembling the geometric model of the fixture onto an inspection system manipulator model;
   selecting at least one mating surface on the component;
   selecting at least one mating surface on the fixture; and
   assembling the geometric model of the component onto the geometric model of the fixture to form a component and fixture assembly using the mating surfaces of the fixture and of the component.

4. The method of claim 3, wherein assembling the geometric model of the component onto the geometric model of the fixture further comprises selecting at least one edge from the component and selecting at least one axis of the fixture for alignment of the component with the fixture.

5. The method of claim 4, further comprising performing at least one of:
   repositioning the component and fixture assembly relative to the inspection system manipulator model;
   orienting the component; and
   offsetting the component relative to the fixture.

6. The method of claim 1, wherein generating the scanplan further comprises:
   selecting at least one inspection surface on the geometric model of the component;
   selecting a probe assembly configuration to inspect the geometric model of the component; and
   generating a probe path for inspecting the inspection surfaces, wherein generating the scanplan is further based on the inspection surfaces and the probe path.

7. The method of claim 6, further comprising performing at least one of:

deselecting at least one of the inspection surfaces; and breaking up at least one of the inspection surfaces.

8. The method of claim 6, further comprising selecting an inspection area on the geometric model of the component.

9. The method of claim 6, further comprising selecting and applying the scanning parameters, wherein the at least one scanning parameter comprise geometric parameters and non-geometric parameters.

10. The method of claim 9, wherein the geometric parameters comprise a plurality of inspection surfaces on the geometrical model of the component.

11. The method of claim 9, wherein the non-geometric parameters are selected from the group consisting of a scan plan velocity parameter, a scan plan step-size parameter, a scan plan direction parameter, an axis tilt parameter, a probe orientation parameter and combinations thereof.

12. The method of claim 1, wherein the scanning parameters are automatically associated with their respective inspection surfaces.

13. The method of claim 1, wherein the validating comprises visualizing the scanplan for at least one of surface inspection overlaps and collision avoidance.

14. A method of inspecting a component, the method comprising;
loading a geometric model of the component;
generating a scanplan of the component based on the geometric model and at least one scanning parameter;
validating the scanplan, wherein validating the scanplan comprises:
automatically retrieving one or more scanning parameters and one or more inspection surfaces from the generated scanplan, automatically loading a component and fixture assembly from the generated scanplan, automatically displaying the one or more inspection surfaces; automatically loading a probe assembly configuration for the one or more inspection surfaces, and visualizing a probe path for the inspection surface, based on the one or more scanning parameters and the probe assembly configuration;
mounting the component on an inspection system manipulator; and
inspecting the component including moving an inspection probe relative to the component using the scanplan.

15. The method of claim 14, wherein the component is held in a fixture mounted on the inspection system manipulator, the method further comprising loading a geometric model of the fixture, wherein generating the scanplan is further based on the geometric model of the fixture.

16. The method of claim 15, wherein loading the geometrical model further comprises:
assembling a geometric model of the fixture onto an inspection system manipulator model;
selecting at least one mating surface on the component;
selecting at least one mating surface on the fixture; and
assembling the geometric model of the component onto the geometric model of the fixture to form a component and fixture assembly using the mating surfaces of the fixture and of the component.

17. The method of claim 14, wherein generating the scanplan further comprises:
selecting at least one inspection surface on the geometric model of the component;
selecting a probe assembly configuration to inspect the geometric model of the component; and
generating a probe path for inspecting the inspection surfaces, wherein generating the scanplan is further based on the inspection surfaces and the probe path.

18. The method of claim 14, wherein the scanning parameters are automatically associated with their respective inspection surfaces.

19. The method of claim 14, wherein the validating comprises visualizing the scanplan for at least one of surface inspection overlaps and collision avoidance.

20. The method of claim 14, wherein the inspection probe comprises an eddy current probe.

21. The method of claim 14, wherein the inspection probe comprises an ultrasonic probe.

* * * * *